United States Patent [19]

Brandes et al.

[11] 4,079,147
[45] Mar. 14, 1978

[54] FUNGICIDALLY ACTIVE DERIVATIVES OF CARBAMIC ACID OXIME-ESTERS OF ISONITROSOCYANOACETIC ACID

[75] Inventors: Wilhelm Brandes, Cologne; Werner Daum, Krefeld, both of Germany

[73] Assignee: Bayer Aktiengesellschaft, Leverkusen, Germany

[21] Appl. No.: 803,340

[22] Filed: Jun. 3, 1977

[30] Foreign Application Priority Data

Jun. 15, 1976 Germany .................... 2626828

[51] Int. Cl.² .............. A61K 31/15; A61K 31/275; C07C 121/14; C07C 121/20
[52] U.S. Cl. .................. 424/304; 260/465.4; 260/566 AC
[58] Field of Search .......... 260/465.4, 566 AC; 424/304

[56] References Cited

U.S. PATENT DOCUMENTS

| | | | |
|---|---|---|---|
| 3,625,987 | 12/1971 | Hubele | 260/465 D |
| 3,769,423 | 10/1973 | Hubele | 424/304 |
| 3,803,320 | 4/1974 | Brechbuhler et al. | 424/304 |
| 3,954,992 | 5/1976 | Davidson | 424/304 X |
| 3,980,693 | 9/1976 | Kuhle et al. | 260/465.4 |
| 4,029,688 | 6/1977 | D'Silva | 260/465.4 |

FOREIGN PATENT DOCUMENTS

| | | |
|---|---|---|
| 2,350,910 | 4/1974 | Germany. |
| 2,436,655 | 2/1975 | Germany. |
| 2,436,654 | 2/1975 | Germany. |
| 1,449,486 | 9/1976 | United Kingdom. |

*Primary Examiner*—Gerald A. Schwartz
*Attorney, Agent, or Firm*—Burgess, Dinklage & Sprung

[57] ABSTRACT

Derivatives of carbamic acid oxime-esters of isonitrosocyanoacetic acid of the formula

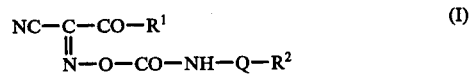

in which
  Q represents a straight or branched hydrocarbon chain with 1 to 11 carbon atoms,
  $R^1$ represents the —$NHR^3$ or —NH—CO—$NH_2$ group or a straight or branched alkoxy group with 1 to 5 carbon atoms,
  $R^2$ represents an alkoxycarbonyl, alkenoxycarbonyl or alkynoxycarbonyl group, in each case with a total of up to 5 carbon atoms, or represents the CN group, and
  $R^3$ represents hydrogen or alkyl with up to 4 carbon atoms which possess fungicidal properties.

11 Claims, No Drawings

FUNGICIDALLY ACTIVE DERIVATIVES OF CARBAMIC ACID OXIME-ESTERS OF ISONITROSOCYANOACETIC ACID

The present invention relates to and has for its objects the provision of particular new derivatives of carbamic acid oxime-esters of isonitrosocyanoacetic acid which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

As has already been known for a long time, zinc ethylene1,2-bis-dithiocarbamate and N-trichloromethyl-thiotetrahydrophthalimide may be used as fungicides in agriculture and in horticulture; amongst commercial products, the said compounds are of great importance (see R. Wegler, "Chemie der Pflanzenschutz- und Schaedlingsbekaempfungsmittel" (Chemistry of Plant Protection Agents and Pesticides), Volume 2, pages 65 and 108, Berlin/Heidelberg/New York (1970)). The action, when low concentrations are used, is however not always satisfactory. Furthermore, these fungicides cannot be employed curatively.

The present invention provides, as new compounds, the carbamic acid oxime-esters of isonitrosocyanoacetic acid derivatives, of the general formula

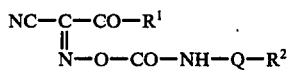    (I)

in which
Q represents a straight or branched hydrocarbon chain with 1 to 11 carbon atoms,
$R^1$ represents the $-NHR^3$ or $-NH-CO-NH_2$ group or a straight or branched alkoxy group with 1 to 5 carbon atoms,
$R^2$ represents an alkoxycarbonyl, alkenoxycarbonyl or alkynoxycarbonyl group, in each case with a total of up to 5 carbon atoms, or represents the CN group, and
$R^3$ represents hydrogen or alkyl with up to 4 carbon atoms.

Preferably, $R^1$ represents the amino, the $H_2N-CO-NH-$ or the methoxy group, Q represents an ethylene, 1,5-pentylene, 1,10-decylene or 1,11-undecylene group and $R^2$ represents the cyano group, the methoxycarbonyl, ethoxycarbonyl, propoxycarbonyl, isopropoxycarbonyl, butoxycarbonyl, isobutoxycarbonyl, sec.-butoxycarbonyl or propargyloxycarbonyl group or an alkenoxycarbonyl group with a total of 4 or 5 carbon atoms.

As oxime derivatives, the compounds according to the invention can exist in two different geometrical structures:

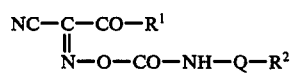    (I)

or

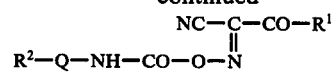    (Ia)

In the text which follows, the spatial structure will not be specified; for the purposes of the present application, the indicated formulae (I) are intended, in each case, also to embrace the corresponding formula according to the spatial structure (Ia).

The compounds according to the present invention exhibit a good fungicidal action. They can be used for protective, curative and eradicative purposes and possess systemic properties. In this respect, they differ advantageously from the dithiocarbamates and N-trichloromethylthiotetrahydrophthalimide, which are only protectively active.

The mere fact of the numerous possibilities of making superior biological use of the compounds according to the invention represents a valuable enrichment of the art. A further important aspect of the present invention is that new active compounds having valuable properties in practice are provided at a point in time where, due to resistance phenomena of older active compounds, there is a pronounced need for new fungicides.

The present invention also provides a process for the preparation of a compound of the formula (I) in which an isonitrosocyanoacetic acid derivative of the general formula

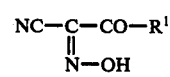    (II), in which
$R^1$ has the above-mentioned meaning, is reacted
(a) with an isocyanate of the general formula $$OCN-Q-R^2 \quad \text{(III)},$$

in which
Q and $R^2$ have the above-mentioned meanings, or
(b) with a carbamic acid halide of the general formula $$Hal-CO-NH-Q-R^2 \quad \text{(IV)},$$

in which
Q and $R^2$ have the above-mentioned meanings and
Hal represents chlorine, bromine or iodine.

If isonitrosocyanoacetamide and ω-cyanopentyl isocyanate are used as starting materials in process variant (a), the course of the reaction is represented by the following equation:

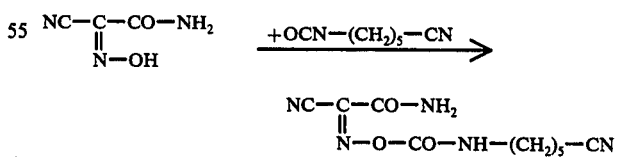

The analogous reaction with ω-cyanopentyl-carbamic acid chloride (process variant (b)) requires the presence of a hydrogen chloride acceptor:

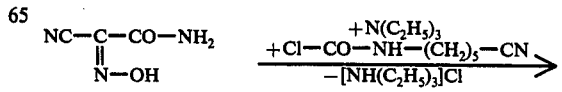

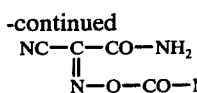

Examples of the isonitrosocyanoacetic acid derivatives (II) to be used in the reaction are 2-cyano-2-oximinoacetamide, 2-cyano-2-oximinoacetyl-urea or 2-cyano-2-oximino-acetic acid methyl ester, ethyl ester, propyl ester, isopropyl ester, n-butyl ester, isobutyl ester, sec.-butyl ester and 2,2-dimethylpropyl ester. The oximino-cyanoacetamides are known and can be prepared from the corresponding cyanoacetylamides by the action of nitrous acid (see Berichte der Deutschen Chemischen Gesellscahft 42, pages 738, 740 and 741 (1909)). The preparation of the oximino-cyanoacetic acid esters is also known; thus, for example, the corresponding cyanoacetic acid esters can be treated with sodium alcoholate and amyl nitrite, or with sodium nitrite in water with addition of sulphuric acid or glacial acetic acid (see Beilsteins Handbuch der Organischen Chemie (Beilstein's Handbook of Organic Chemistry), H3, page 775).

Examples to be mentioned, of the isocyanates of the formula (III) to be used in the reaction, are: ω-cyanoethyl isocyanate, 1-cyano-1-methyl-ethyl isocyanate, ω-cyanopropyl isocyanate, ω-cyanopentyl isocyanate, ω-cyanohexyl isocyanate, ω-cyanooctyl isocyanate, ω-cyanononyl isocyanate, ω-cyanodecyl isocyanate, ω-cyanoundecyl isocyanate, methoxycarbonylmethyl isocyanate, ethoxycarbonylmethyl isocyanate, butoxycarbonylethyl isocyanate, isobutoxycarbonylethyl isocyanate, 1-methoxycarbonyl-1-methyl-ethyl isocyanate, 1-propoxycarbonyl-1-methylethyl isocyanate, 1-ethoxycarbonyl-1-ethyl-ethyl isocyanate, 1-isobutoxycarbonyl-1-ethyl-ethyl isocyanate, methoxycarbonyl-propyl isocyanate, methoxycarbonyl-pentyl isocyanate, isopropoxycarbonyl-pentyl isocyanate, sec.-butoxycarbonyl-pentyl isocyanate, allyloxycarbonyl-pentyl isocyanate, propargyloxycarbonyl-pentyl isocyanate, 2-ethoxycarbonyl-2-ethyl-butyl isocyanate, γ-ethoxycarbonyloctyl isocyanate, methoxycarbonyl-decyl isocyanate, ethoxycarbonyl-decyl isocyanate, propoxycarbonyl-decyl isocyanate, butoxycarbonyl-decyl isocyanate, allyloxycarbonyl-decyl isocyanate, but-2-enyloxycarbonyl-decyl isocyanate, methoxycarbonyl-undecyl isocyanate and allyloxycarbonylundecyl isocyanate.

The majority of the isocyanates to be employed as starting materials are known and are prepared in accordance with generally known processes, for example by reacting primary amines with phosgene in inert solvents, by the so-called "Hofmann's degradation" of the acid amides and by other methods customary in the laboratory (see, for example, Liebigs Ann. Chem. 562, 75–136 (1949), U.S. Pat. No. 2,803,208, U.S. Pat. No. 3,673,210, column 16, lines 67–74, and DT-OS (German Published Specification) No. 1,913,273).

Instead of the isocyanates of the formula (III) given by way of example above, it is in each case possible to use the corresponding carbamic acid halide of the formula (IV). The preparation of these compounds, can be carried out in known manner in accordance with processes customary in the laboratory, for example, by addition of hydrogen halide to the corresponding isocyanates of the formula (III) as ilustrated in preparative Example 6 hereinbelow.

Process variant (a) according to the invention is advantageously carried out in a diluent. Any inert organic solvent can be used for this purpose, although it is preferred to use dimethylsulphoxide; dimethylformamide; dimethylacetamide; ethyl acetate; ketones, such as, for example, acetone, methyl ethyl ketone and diethyl ketone; ethers, such as, for example, tetrahydrofuran; chlorinated hydrocarbons, such as, for example, methylene chloride and chloroform; nitriles, such as, for example, acetonitrile and benzonitrile; and aromatics, such as, for example, toluene and chlorobenzene.

Basic catalysts can be used as auxiliaries in process variant (a); examples are tertiary amines, such as triethylamine or pyridine, and also tin 2-ethyl-hexanoate. Tertiary amines can also, at the same time, serve as solvents.

In process variant (a), the reaction temperatures can be varied within a fairly wide range. In general, the reaction is carried out at from −20° to +120° C, preferably from +20° to 70° C.

The working up of the reaction products obtained according to process variant (a) can be effected by separating off the products obtained, which are mostly sparingly soluble, by a simple filtration process, or causing them to separate out by adding petroleum ether or dibutyl ether to the reaction mixtures. If a water-miscible solvent is present, the compounds according to the invention can also be precipitated by adding water.

Process variant (b) according to the invention is carried out in an inert organic solvent. Here, the solvents mentioned when discussing process variant (a) can be used.

Auxiliaries used in process variant (b) are customary inorganic or organic acid-binding agents. Amongst inorganic acid-binding agents, alkali metal carbonates, such as potassium carbonate or sodium carbonate, should be mentioned, as well as sodium tetraborate (borax) or trilithium phosphate.

The reaction temperatures in process variant (b) correspond to the reaction temperatures stated above with reference to process variant (a).

Working up is carried out by first eluting the halides formed with water in the cold; thereafter the procedure followed is as indicated above for process variant (a).

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention can be used against parasitic fungi which attack above-ground parts of plants or attack the plants through the soil, as well as against seed-borne pathogens. Accordingly, they can also be used for the treatment of soil and for the treatment of seed.

The active compounds in particular exhibit a high protective and curative activity against Phycomycetes.

The active compounds according to the invention not only exhibit the good properties of outstanding commercial preparations, but in addition also possess advantages. These reside, above all, in the ability of the compounds according to the invention to penetrate into the plant. They can be taken up by the surface of the seed, by the roots and also by above-ground organs of the plant, after external application. Furthermore they possess the advantageous ability of coming into effect locosystemically, that is to say they exert a depth effect in plant tissue and thereby eliminate fungal pathogens which have already penetrated into the tissue of the host plant.

The active compounds according to the instant invention can be utilized, if desired, in the form of the usual formulations or compositions with conventional inert (i.e. plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellents which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl polyglycol ethers, magnesium stearate, sodium oleate, etc.); and/or dispersing agents, such as lignin, sulfite waste liquors, methyl cellulose, etc.

In addition to the above formulation possibilities, it should be noted that the compounds according to the invention can be formulated together with sucrose, dextrose, dextrins, anhydrous calcium sulphate or calcium sulphate hemihydrate.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematicides, bactericides, rodenticides, fertilizers, herbicides, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the concentrations of active compound in the use forms can be varied within a fairly wide range. They are in general from 0.5 to 0.0005 percent by weight, preferably from 0.2 to 0.001 percent.

In the treatment of seed, amounts of active compound of 0.01 to 50 g per kilogram of seed, preferably 0.5 to 5 g, are generally employed.

For the treatment of soil, amounts of active compound of 1 to 1,000 g per cubic meter of soil, preferably of 10 to 200 g, are generally employed.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown, or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phytophthora test (tomatoes)/curative

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were inoculated with an aqueous spore suspension of *Phytophthora infestans*. The plants remained for 7 hours at 20° C and a relative atmospheric humidity of 100%.

After a short drying-off time, the plants were sprayed with the spray liquid, prepared in the manner described above, until dripping wet, and were then brought into a humidity chamber at 100% atmospheric humidity and 18° to 20° C.

After 5 days the infection of the tomato plants was determined. The assessment data obtained were converted to percent infection: 0% meant no infection; 100% meant that the plants were totally infected.

The active compounds, the concentrations of the active compounds and the results can be seen from the following table:

Table 1

| Active compound | *Phytophthora* test (tomatoes)/curative Infection in % at an active compound concentration of 0.025% |
|---|---|
| $CH_2-NH-CS-S$<br>$\phantom{CH_2-NH-CS-}$Zn<br>$CH_2-NH-CS-S$<br>(known) (A) | 61 |
| $NC-C-CO-NH_2$<br>$\phantom{NC-}\|\|$<br>$\phantom{NC-}NOH$<br>(known) (B) | 7 |
| $NC-C-CO-OCH_3$<br>$\phantom{NC-}\|\|$<br>$\phantom{NC-}N-O-CO-NH-(CH_2)_5-CN$<br>(6) | 7 |
| $NC-C-CO-NH-CO-NH_2$<br>$\phantom{NC-}\|\|$<br>$\phantom{NC-}N-O-CO-NH-(CH_2)_5-CN$<br>(2) | 4 |
| $NC-C-CO-NH_2$<br>$\phantom{NC-}\|\|$<br>$\phantom{NC-}N-O-CO-NH-(CH_2)_5-CN$<br>(1) | 9 |
| $NC-C-CO-NH_2$<br>$\phantom{NC-}\|\|$<br>$\phantom{NC-}N-O-CO-NH-(CH_2)_{11}-CO-OCH_3$<br>(3) | 11 |
| $NC-C-CO-NH_2$<br>$\phantom{NC-}\|\|$<br>$\phantom{NC-}N-O-CO-NH-(CH_2)_5-CO-OCH_3$<br>(5) | 1 |
| $NC-C-CO-NH_2$<br>$\phantom{NC-}\|\|$<br>$\phantom{NC-}N-O-CO-NH-(CH_2)_{11}-CN$<br>(4) | 10 |

EXAMPLE 2

Phytophthora test (tomatoes)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C and at a relative atmospheric humidity of 70%. The tomato plants were then inoculated with an aqueous spore suspension of *Phytophthora infestans*. The plants were brought into a moist chamber with an atomspheric humidity of 100% and a temperature of 18°–20° C.

After 5 days the infection of the tomato plants was determined. The assessment data were converted to percent infection: 0% meant no infection; 100% meant that the plants were totally infected.

The active compounds, the concentrations of the active compounds and the results can be seen from the following table:

Table 2

Phytophthora test (tomatoes)/protective

| Active compound | Infection in % at an active compound concentration of 0.0025% |
|---|---|
| CH$_2$—NH—CS—S<br>\|　　　　　　　　　＼Zn<br>CH$_2$—NH—CS—S／<br><br>(known) (A) | 41 |
| NC—C—CO—NH$_2$<br>　‖<br>　N—O—CO—NH—(CH$_2$)$_{11}$—CN<br><br>(4) | 36 |
| NC—C—CO—NH$_2$<br>　‖<br>　N—O—CO—NH—(CH$_2$)$_5$—CO—OCH$_3$<br><br>(5) | 25 |

EXAMPLE 3

Phytophthora test (tomatoes)/systemic

Solvent: 4.7 parts by weight of acetone
Emulsifier: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated additions.

Tomato plants grown in standard soil and having 2 to 4 foliage leaves were watered three times in the course of one week with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmospheric humidity of 100% and a temperature of 18° to 20° C. After 5 days, the infection of the tomato plants was determined. The assessment data obtained were converted to percent infection. 0% denoted no infection and 100% denoted that the plants were totally infected.

The active compounds, the concentrations of the active compound and the results can be seen from the following table:

Table 3

Phytophthora test (tomatoes)/systemic

| Active compound | Infection in % at an active compound concentration of 100 ppm |
|---|---|
| NC—C—CO—NH$_2$<br>　‖<br>　NOH<br><br>(known) (B) | 0 |
| NC—C—CO—OCH$_3$<br>　‖<br>　N—O—CO—NH—(CH$_2$)$_5$—CN<br><br>(6) | 1 |
| NC—C—CO—NH$_2$<br>　‖<br>　N—O—CO—NH—(CH$_2$)$_5$—CN<br><br>(1) | 0 |
| NC—C—CO—NH$_2$<br>　‖<br>　N—O—CO—NH—(CH$_2$)$_5$—CO—O—CH$_3$<br><br>(5) | 0 |

EXAMPLE 4

Phytotoxicity test

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water, which contained the stated additives. Young tomatoes were sprayed with the spray liquor until dripping wet. After drying off, the plants were set up in a greenhouse at a temperature of +20° C and about 70% relative atmospheric humidity.

The damage to the plants was evaluated repeatedly. The evaluation was made in accordance with a scheme of rating from 1 to 9.

1 denoted no damage
9 denoted that the plants were totally damaged or dead. The period of observation was, as a rule, 4 days.

The active compounds, active compound concentrations and results can be seen from the following table:

Table 4

Phytotoxicity test

| Active compound | Damage at an active compound concentration of 0.2% |
|---|---|
| NC—C—CO—NH$_2$<br>　‖<br>　NOH<br><br>(known) (B) | 8 |
| NC—C—CO—OCH$_3$<br>　‖<br>　N—O—CO—NH—(CH$_2$)$_5$—CN<br><br>(6) | 2 |
| NC—C—CO—NH—CO—NH$_2$<br>　‖<br>　N—O—CO—NH—(CH$_2$)$_5$—CN<br><br>(2) | 3 |

Table 4-continued
Phytotoxicity test

| Active compound | Damage at an active compound concentration of 0.2% |
|---|---|
| NC—C(=N—O—CO—NH—(CH₂)₅—CO—OCH₃)—CO—NH₂ (5) | 5 |

The process of the present invention is illustrated by the following preparative examples:

EXAMPLE 5

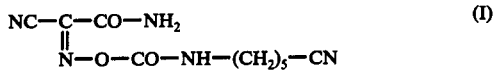

(I)

20 g (0.175 mol) of isonitrosocyanoacetamide were suspended in 50 ml of acetonitrile. 25.3 g (0.183 mol) of ω-cyanopentyl isocyanate were next added, followed by 50 mg of triethylenediamine as the catalyst. The reaction was exothermic and after it had subsided the mixture was kept for a further 3 hours at 60° C. It was then cooled and the sparingly soluble crystals were separated off and washed with acetonitrile. 42.5 g (96% of theory) of 2-cyano-2-(ω-cyanopentylamino-carbonyloximino)-acetamide of melting point 150° C were obtained.

IR spectra (KBr): 3,340, 2,160, sh 3,200–3,230, 1,770, 1,700 and 1,524 cm⁻¹.

The following compounds of the general formula (I) could be prepared analogously:

Table 5

| Compound No. | R¹ | Q | R² | Melting point (° C) |
|---|---|---|---|---|
| 2 | NH—CO—NH₂ | (CH₂)₅ | CN | 167 (with decomposition) |
| 3 | NH₂ | (CH₂)₁₁ | CO—OCH₃ | 102 |
| 4 | NH₂ | (CH₂)₁₁ | CN | 102 |
| 5 | NH₂ | (CH₂)₅ | CO—OCH₃ | 124 |
| 6 | OCH₃ | (CH₂)₅ | CN | 93 |

EXAMPLE 6

The products of Example 5 can be prepared by process variant (b) accordong to the invention, which requires the carbamic acid halides of the formula (IV), i.e. the carbamic acid halide counterparts of the isocyanates of formula (III). The synthesis of ω-cyanopentyl-carbamic acid chloride may be given as an example of their preparation:

Regarding the preparation of the intermediate products

For process variant (b) according to the invention, the carbamic acid halides of the formula (IV) are required. The synthesis of ω-cyanopentyl-carbamic acid chloride may be given as an example of their preparation:

Cyanopentyl isocyanate (known from Liebigs Ann. Chem. 562, 104 (1949)) was first placed in the vessel, while cooling with ice. Hydrogen chloride was passed in until saturation was reached and thereafter hydrogen chloride was passed through the liquid reaction product for a further 20 minutes. After this had been completed, the reaction mixture was kept for 2 hours at a temperature of 30° C under a pressure of 10 mm Hg and at the same time a slight stream of nitrogen was passed through the liquid reaction product.

The ω-cyanopentyl-carbamic acid chloride obtained as described had a refractive index $n_D^{20}$ of 1.4778–1.4781.

Other end products of formula (I) which can be prepared either from the isocyanates or carbamic acid chlorides include the following:

Table 6

| R' | Q | R² |
|---|---|---|
| NH₂ | (CH₂)₂ | CO—O—C₄H₉-iso |
| NH₂ | (CH₂)₁₀ | CO—O—CH₂—CH=CH₂ |
| NH₂ | CH₂ | CO—O—C₂H₅ |
| NH₂ | (CH₂)₅ | CO—O—CH₂—C≡CH |
| NH₂ | —CH₂—C(C₂H₅)₂— | CO—O—C₂H₅ |
| and the like. | | |

It will be appreciated that the instant specification and examples are set forth by way of illustration and not limitation, and that various modifications and changes may be made without departing from the spirit and scope of the present invention.

What is claimed is:

1. A carbamic acid oxime-ester of an isonitrosocyanoacetic acid derivative of the formula

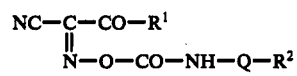

in which
Q represents a straight or branched hydrocarbon chain with 1 to 11 carbon atoms,
R¹ represents the —NHR³ or —NH—CO—NH₂ group or a straight or branched alkoxy group with 1 to 5 carbon atoms,
R² represents an alkoxycarbonyl, alkenoxycarbonyl or alkynoxycarbonyl group, in each case with a total of up to 5 carbon atoms, or represents the CN group, and
R³ represents hydrogen or alkyl with up to 4 carbon atoms.

2. A compound according to claim 1, in which R¹ represents the amino, the H₂N—CO—NH— or the methoxy group, Q represents an ethylene, 1,5-pentylene, 1,10-decylene or 1,11-undecylene group, and R² represents the cyano group, the methoxycarbonyl, ethoxycarbonyl, propoxycarbonyl, isopropoxycarbonyl, butoxycarbonyl, isobutyoxycarbonyl, sec.-butyoxycarbonyl or propargyloxycarbonyl group or an alkenoxycarbonyl group with a total of 4 or 5 carbon atoms.

3. The compound according to claim 1, wherein such compound is 2-cyano-2-(ω-cyanopentylamino-carbonyloximino)acetamide of the formula

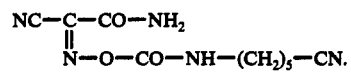

4. The compound according to claim 1, wherein such compound is 1-(2-cyano-2-(ω-cyanopentylamino-carbonyloximino)-acetyl-urea of the formula

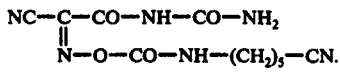

5. The compound according to claim 1, wherein such compound is 2-cyano-2-(ω-methoxycarbonyl-undecylaminocarbonyloximino)-acetamide of the formula

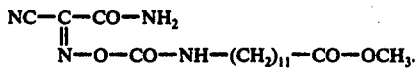

6. The compound according to claim 1, wherein such compound is 2-cyano-2-(ω-cyanoundecylamino-carbonyloximino)acetamide of the formula

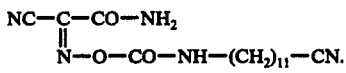

7. The compound according to claim 1, wherein such compound is 2-cyano-2-(ω-methoxycarbonyl-pentylamino-carbonyloximino)-acetamide of the formula

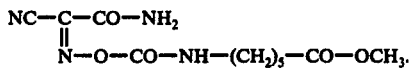

8. The compound according to claim 1, wherein such compound is 2-cyano-2-(ω-cyanopentylamino-carbonyloximino)acetic acid methyl ester of the formula

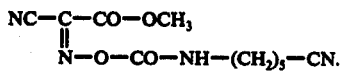

9. A fungicidal composition containing as active ingredient a fungicidally effective amount of a compound according to claim 1 in admixture with a diluent.

10. A method of combating fungi which comprises applying to the fungi, or to a habitat thereof, a fungicidally effective amount of a compound according to claim 1.

11. The method according to claim 10 in which said compound is
2-cyano-2-(ω-cyanopentylamino-carbonyloximino)acetamide,
1-(2-cyano-2-(ω-cyanopentylamino-carbonyloximino)-acetyl-urea.
2-cyano-2-(ω-methoxycarbonyl-undecyclamino-carbonyloximino)-acetamide,
2-cyano-2-(ω-cyanoundecylamino-carbonyloximino)-acetamide,
2-cyano-2-(ω-methoxycarbonyl-pentylamino-carbonyloximino)-acetamide, or
2-cyano-2-(ω-cyanopentylamino-carbonyloximino)-acetic acid methyl ester.